(12) United States Patent
Baecke et al.

(10) Patent No.: US 9,272,110 B2
(45) Date of Patent: Mar. 1, 2016

(54) REPLACEABLE NASAL INTERFACE SYSTEM

(75) Inventors: Martin Baecke, Dessau-Rosslau (DE); Marcel Borgward, Oedheim (DE); Uwe Schwerdtfeger, Güsten (DE); Stuart Allan Karten, Venice, CA (US); Dennis Lynn Schroeder, Los Angeles, CA (US); Jeffrey Walter Bentzler, Playa Del Rey, CA (US)

(73) Assignee: inSleep Technologies, LLC, Weston, FL (US)

( * ) Notice: Subject to any disclaimer, the term of this patent is extended or adjusted under 35 U.S.C. 154(b) by 688 days.

(21) Appl. No.: 13/534,984

(22) Filed: Jun. 27, 2012

(65) Prior Publication Data

US 2013/0008450 A1 Jan. 10, 2013

Related U.S. Application Data

(60) Provisional application No. 61/501,444, filed on Jun. 27, 2011.

(51) Int. Cl.
| | |
|---|---|
| *A61M 11/00* | (2006.01) |
| *A61M 16/06* | (2006.01) |
| *A61F 5/56* | (2006.01) |
| *A61M 16/08* | (2006.01) |
| *A61M 16/00* | (2006.01) |

(52) U.S. Cl.
CPC ............... *A61M 16/06* (2013.01); *A61F 5/56* (2013.01); *A61M 16/0683* (2013.01); *A61M 16/0816* (2013.01); *A61M 16/0875* (2013.01); *A61M 2016/0027* (2013.01); *A61M 2210/0618* (2013.01)

(58) Field of Classification Search
CPC ................. A61M 2210/0618; A61M 16/0816; A61M 16/06; A61M 5/56; A61M 16/0683; A61M 16/0875; A61M 2016/0027
USPC ............ 128/207.13, 207.18, 202.27, 205.25, 128/206.21, 206.24, 206.27, 206.28, 207.11
See application file for complete search history.

(56) References Cited

U.S. PATENT DOCUMENTS

| | | | | |
|---|---|---|---|---|
| 6,044,844 | A * | 4/2000 | Kwok et al. | 128/207.11 |
| 6,196,223 | B1 | 3/2001 | Belfer et al. | |
| 6,247,470 | B1 * | 6/2001 | Ketchedjian | 128/200.28 |
| 6,394,142 | B1 | 5/2002 | Woelfel et al. | |
| 7,059,328 | B2 * | 6/2006 | Wood | 128/207.18 |
| 7,302,950 | B2 | 12/2007 | Berthon-Jones et al. | |
| 7,556,043 | B2 | 7/2009 | Ho et al. | |
| 7,870,859 | B2 * | 1/2011 | Barnett et al. | 128/204.24 |
| 2006/0189961 | A1 | 8/2006 | Miyahara | |
| 2006/0283460 | A1 * | 12/2006 | Brown et al. | 128/206.24 |
| 2008/0276941 | A1 * | 11/2008 | Doty et al. | 128/205.28 |

(Continued)

OTHER PUBLICATIONS

International Search Report and Written Opinion for International Application No. PCT/US12/44420 mailed Oct. 2, 2012.

*Primary Examiner* — Steven Douglas
(74) *Attorney, Agent, or Firm* — Kevin P. Crosby; GrayRobinson, P.A.

(57) ABSTRACT

A replaceable nasal interface system including a molded air tube having a generally D-shaped cross section, and including first and second lumens. The system further includes a base member operatively connected to and in fluid communication with the molded air tube; and a nasal interface operatively connected to the base member.

2 Claims, 14 Drawing Sheets

(56) References Cited

U.S. PATENT DOCUMENTS

2009/0223518 A1* 9/2009 Kwok et al. ............ 128/205.25
2010/0318069 A1* 12/2010 Hall et al. .................... 604/535
2012/0266890 A1 10/2012 Baecke et al.

* cited by examiner

REPLACEABLE NASAL INTERFACE SYSTEM

CROSS-REFERENCE TO RELATED APPLICATIONS

This application claims the benefit of U.S. provisional patent application No. 61/501,444, entitled Nasal Interface, filed on Jun. 27, 2011, the entire disclosure of which is incorporated herein by reference.

TECHNICAL FIELD

The present disclosure generally relates to a breathing apparatus, and more particularly to a simple and replaceable nasal interface system for a breathing apparatus that may be used in connection with reducing snoring.

BACKGROUND OF THE DISCLOSURE

Snoring is an affliction that affects many people. Snoring may be an ongoing, regular problem, or may occur intermittently or occasionally. Snoring may result in various problems, both to the person snoring as well as those around the person snoring. For example, snoring has been linked to sleep deprivation, in which the sleeping patterns of the person snoring may be disrupted. Such sleep deprivation may result in daytime drowsiness, lack of focus, as well as other problems. There are a number of other breathing disorders including, but not limited to, OSA, COPD, and Asthma that could be aided by the use of a supplemental breathing apparatus.

As will be recognized, an interface between a user and any such supplemental breathing apparatus is essential. A common interface is a nasal interface. Due to contact with the user, maintenance such as washing and replacement are common practices for user. Thus, there is a need for an easily replaceable nasal interface.

SUMMARY OF THE DISCLOSURE

According to a first implementation, a replaceable nasal interface system can comprise a molded air tube having a generally D-shaped cross section, and including first and second lumens; a base member operatively connected to and in fluid communication with the molded air tube; and a nasal interface operatively connected to the base member.

The details of one or more implementations are set forth in the accompanying drawings and the description below. Other features will become apparent from the description, the drawings, and the claims.

DETAILED DESCRIPTION OF PREFERRED EMBODIMENTS

Figure 1:
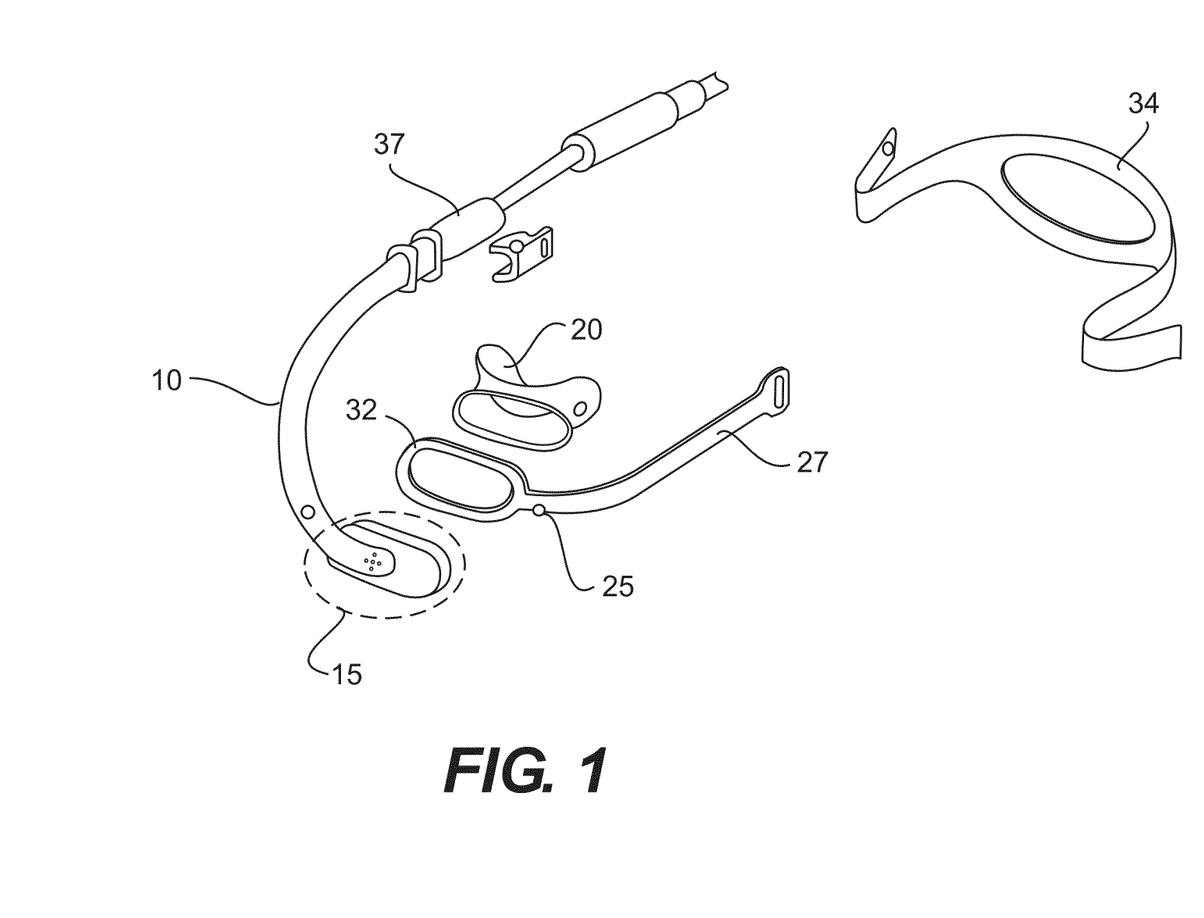
FIG. 1 perspective view of an illustrative embodiment of the present disclosure.

FIG. 1 perspective view of an illustrative embodiment of the present disclosure. The replaceable nasal interface system illustrated in FIG. 1 includes a molded air tube 10. As seen in the exemplary embodiment shown in FIG. 3B, the molded air tube 10 has a generally D-shape. The molded air tube 10 includes, in the illustrated example, a first lumen 30 and a second lumen 35. The first lumen 30 can be used in some embodiments to supply air to a base 15. The second lumen 35 can be used to place the nasal interface system in fluid communication with a sensor, such as a pressure sensor. As shown in FIGS. 1, 2, 3A, and 4A, in some embodiments of the disclosure, the molded air tube 10 can be molded to generally conform to the contours of a user's face.

Referring to FIG. 1, the molded air tube 10 is operatively connected in fluid communication with the base member 15. The base member 15 can have any desired shape. In an illustrative embodiment, the base member 15 can have a generally concave shape to define a space within the boundaries of the base member 15. The base member has a shape to fittingly engage a nasal interface 20. Examples of fittingly engaging include various snap and pressure fit engagements. Such mechanical couplings are well know to those skilled in the art and are therefore not discussed in detail.

In an exemplary embodiment, the nasal interface 20 can comprise a flexible material and have portion with a shape that complements a corresponding shape in the base member 15 so as to mechanically couple the base member 15 and the nasal interface 20. In an exemplary nasal interface is disclosed in U.S. patent application Ser. No. 13/280,650, entitled Butterfly Nasal Interface, the disclosure of which is hereby incorporated by reference.

Figures 3A, 3B:
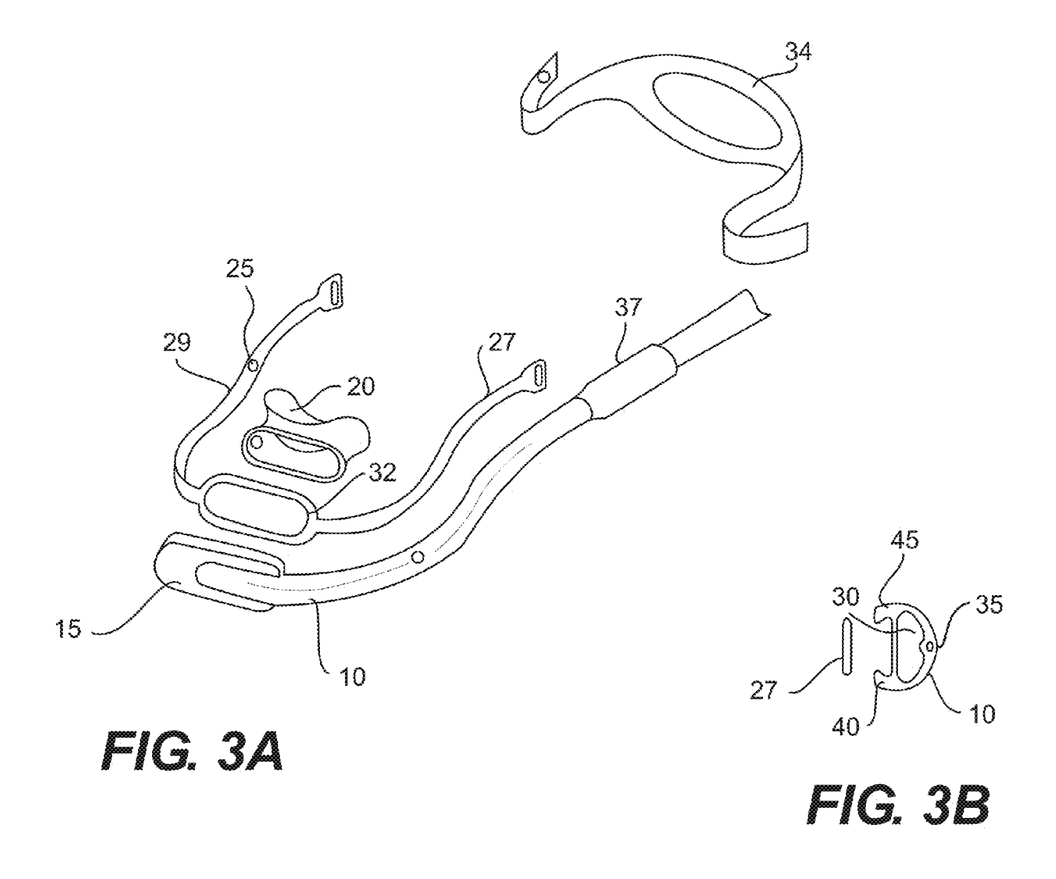
FIG. 3A s a perspective view of another illustrative embodiment of the present disclosure.
FIG. 3B is cross-sectional view of the FIG. 3A embodiment.

The exemplary embodiment shown in FIG. 1 can also include a flexible molded support structure 25. As show in the FIG. 1 embodiment, the flexible molded support structure 25 has flat opposing faces, which is also shown in the cross section view of FIG. 3B. The illustrated flexible molded support structure 25 shown in FIG. 1 has one strap portion 27. Another embodiment of the flexible molded support structure 25 is shown in FIG. 3A, and includes two strap portions 27 and 29. The strap portion 29 also has opposing flat surfaces as does the strap portion 27 discussed above.

The flexible molded support structure includes an open portion 32. In one embodiment, the open portion can fit about the nasal interface 20. In other embodiments, the open portion 32 can engage the nasal interface 20 and the base member 15 so as to couple the base member 20 and the nasal interface 20. The open portion 32 can function to provide a pressure to the nasal interface 20 when combined with a strap 34. This pressure can hold the nasal interface 20 against a user's nose. The use of a strap 34, and variations thereof, is well known in the art to hold a nasal interface, such as the nasal interface 20, against a user's nose.

Figure 2:
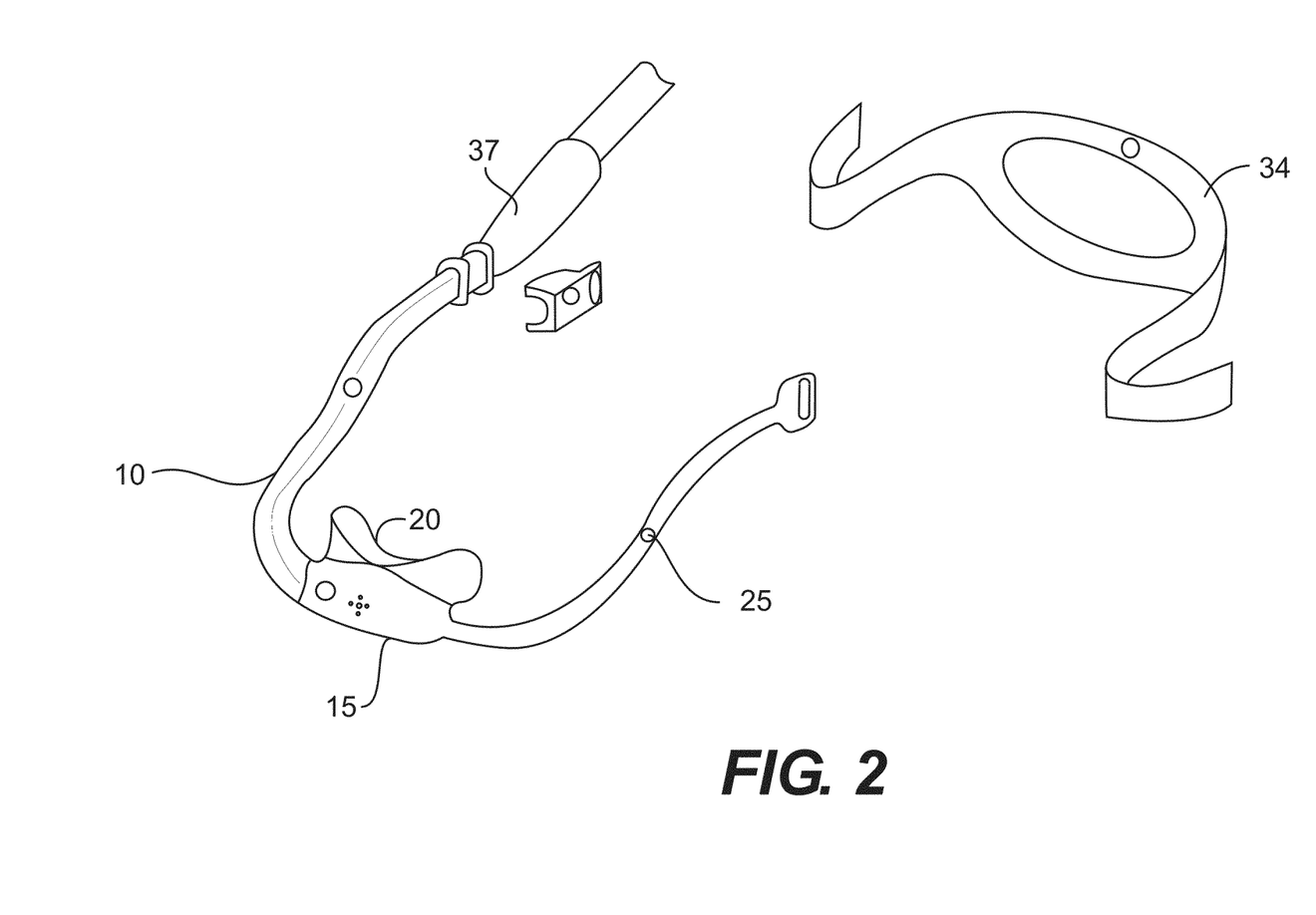
FIG. 2 is a perspective view of another illustrative embodiment of the present disclosure.

FIG. 2 is a perspective view of another illustrative embodiment of the present disclosure. In the FIG. 2 embodiment, the base member 15 and nasal interface 20 comprise a single molded structure. The FIG. 2 embodiment also includes the molded air tube 10 and strap portion 25. I accordance with the illustrate embodiment, the base member 15, nasal interface 20, molded air tube 10, and molded support structure 25 comprise a single molded structure. The nasal interface 20 in the FIG. 2 embodiment can also be fused, such as by ultrasonic welding, to the base member 15 so as to form a unified seamless structure. While not preferable, molded air tube 10 and/or the molded support structure 25 could also be similarly fused to the base portion 15 to form a unified seamless structure.

FIG. 3A s a perspective view of another illustrative embodiment of the present disclosure. The FIG. 3A embodiment is similar to the FIG. 1 embodiment discussed above. As noted the molded support structure 25 shown in FIG. 3A includes two strap portions 27 and 29.

FIG. 3B is cross-sectional view of the FIG. 3A embodiment. In cross-sectional view of FIG. 3B, the vertical dimension and the thickness of the strap portion 27 are sized to snap into a portion of the molded air tube 10 defined by tabs 40 and 45. This arrangement allows the molded air tube 10 to be easily removed from the molded support structure 25. FIG. 3B also illustrates and example internal structure of the molded air tube. 10. In the FIG. 3B example, the molded air tube 10 includes a first lumen 30, which can be used to supply air to the nasal interface 20. The FIG. 3B example also includes a second lumen 35, which can be used to measure pressure at an end point of the second lumen 35. For example, the second lumen 35 could end at or within the base member 15 and provide a representation of the pressure at the nasal interface 20.

Figures 4A, 4B, 4C:
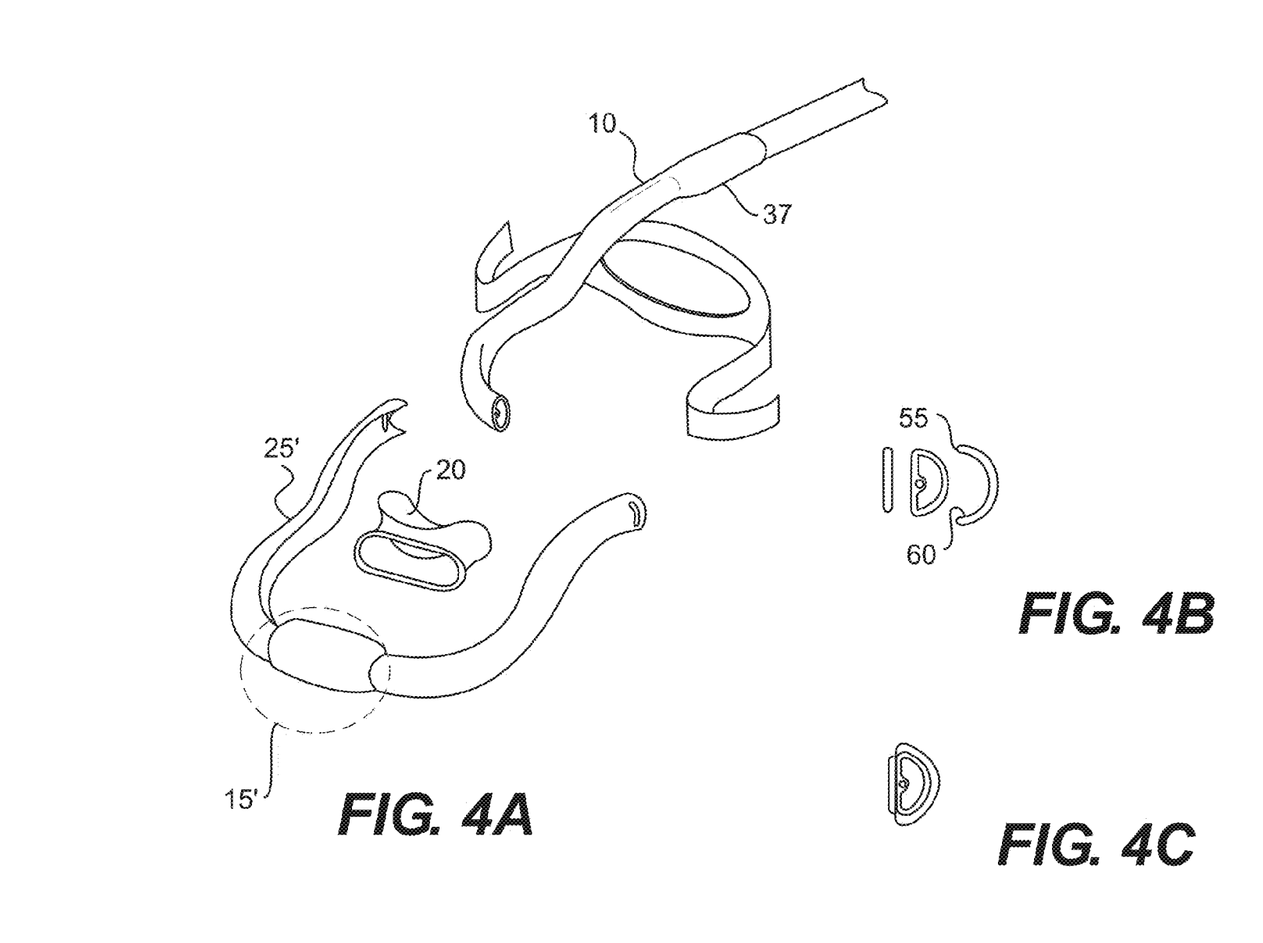
FIG. 4A is a perspective view of another illustrative embodiment of the present disclosure.
FIG. 4B is cross-sectional view of the FIG. 4A embodiment.
FIG. 4C is cross-sectional view of the FIG. 4A embodiment.

FIG. 4A is a perspective view of another illustrative embodiment of the present disclosure. The FIG. 4A embodiment includes a modified molded support structure 25' and a modified base member 15'. The modified molded support structure 25' can be attached to the modified base member 15', such as by fitting into (e.g., press fit) the modified base member 15' or via a mechanical attachment such a snap type attachment. The modified molded support structure 25' could also be molded with or bonded to the modified base member 15'.

Referring to FIG. 4B, the molded air tube 10 fits into the modified support structure 25'. In the FIG. 4B illustrative embodiment, the molded air tube 10 is held in place by protrusions 55 and 60. As those skilled in the art recognize, any other mechanism can be used to hold the molded air tube 10 in place.

Figure 5A:
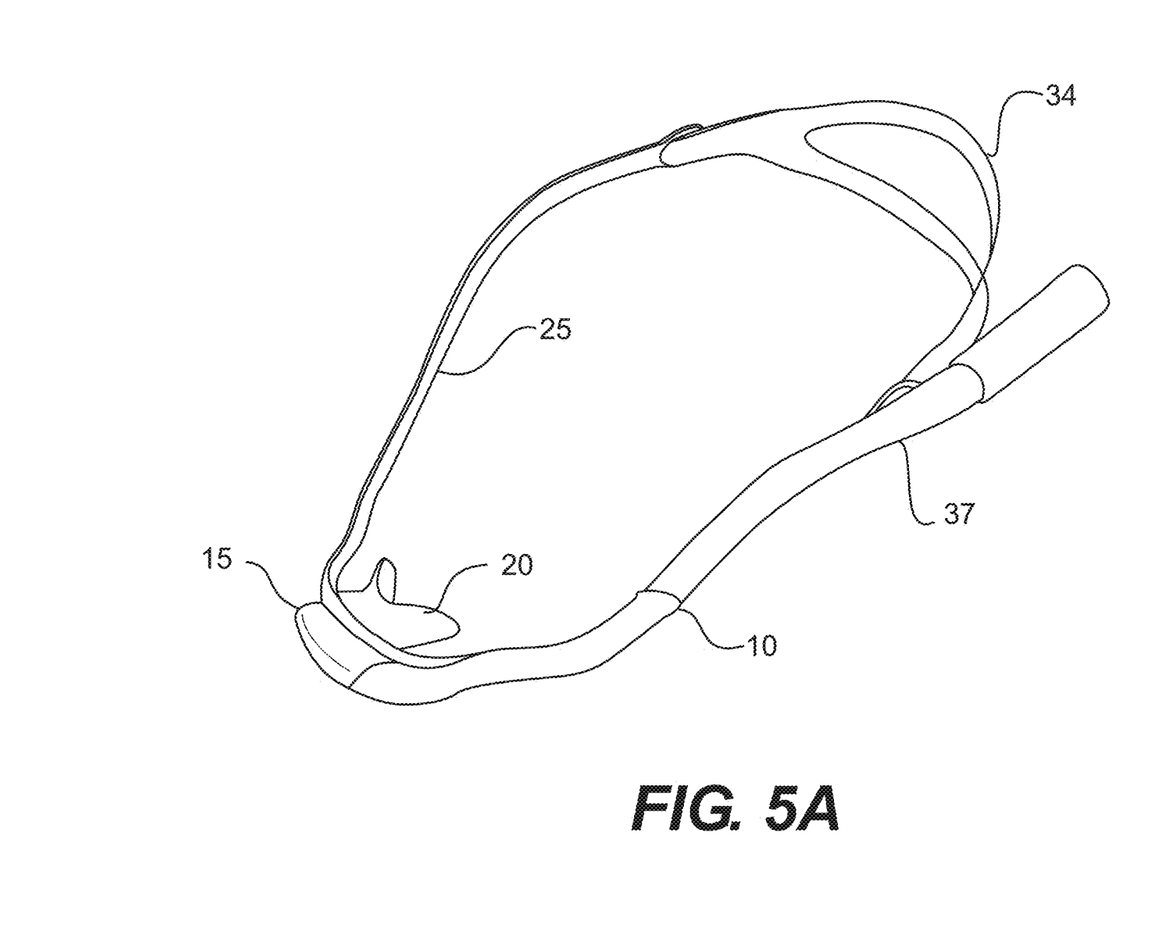
FIG. 5A is a perspective view of another illustrative embodiment of the present disclosure.
Figure 5B:
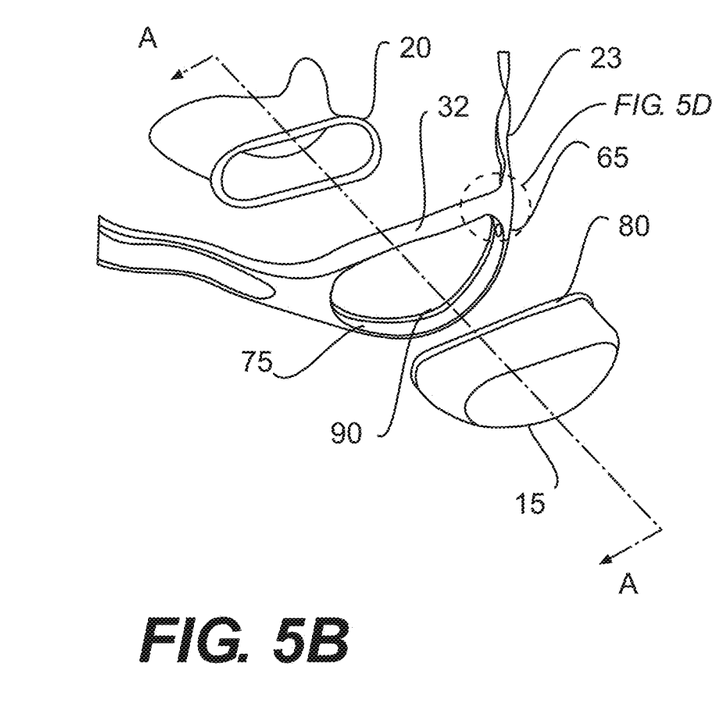
FIG. 5B is an exploded perspective view of the FIG. 5A embodiment.
Figure 5C:
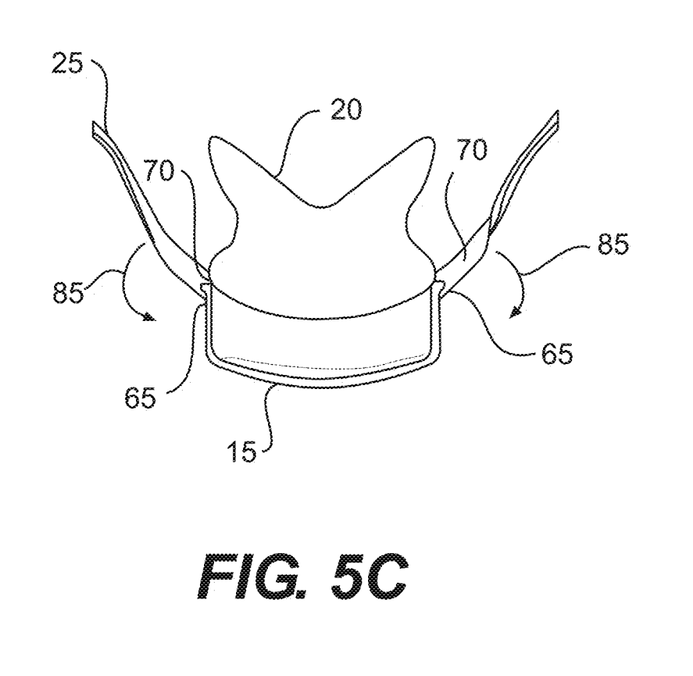
FIG. 5C is a cross-sectional view of the FIG. 5A embodiment.
Figure 5D:
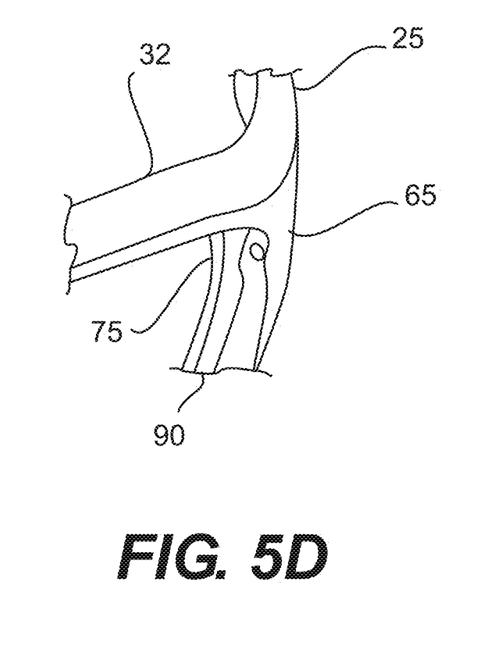
FIG. 5D depicts an enlargement of a portion of FIG. 5B.

FIG. 5A is a perspective view of another illustrative embodiment of the present disclosure. Referring to FIGS. 5B-5D, a lip 70 of the nasal interface 20 fits on a ledge 75 of the molded support structure 25. As seen in FIG. 5C, a lip 80 of the base member 15 also fits on the ledge 75. In the illustrated embodiment, the lip 80 of the base member 15 is held in place by snap tabs 65. This presses the lip 70 of the nasal interface and the lip 80 of the base member 15 together on the ledge 75 against a back portion of 90 of the ledge 75; with the snap tabs 65 holding them in place within the molded support structure 25. By flexing the molded support structure 25 in the direction of the arrows the nasal interface 20 can be released from the ledge 75. Flexing the molded support structure 25 also aids in positioning the nasal interface 20 on the ledge 75. Flexing the molded support structure 25 in a direction opposite the arrows 85 tends to move the snap tabs 65 away from the base member 15 allowing it to be freed from the molded support structure 25.

Figure 6:
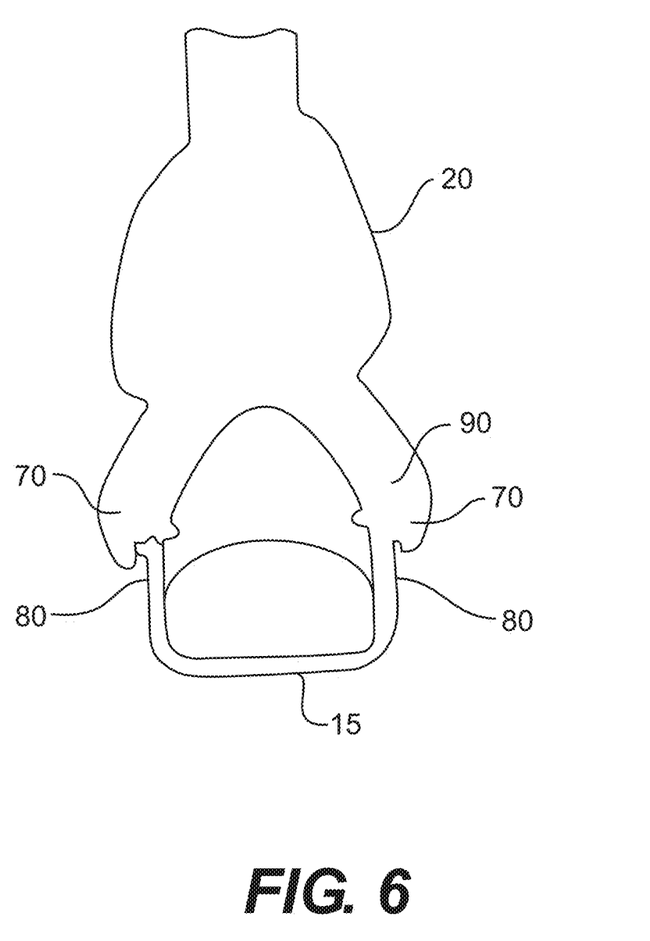
FIG. 6 is a cross-sectional view of the FIG. 5A embodiment.
Figure 7:
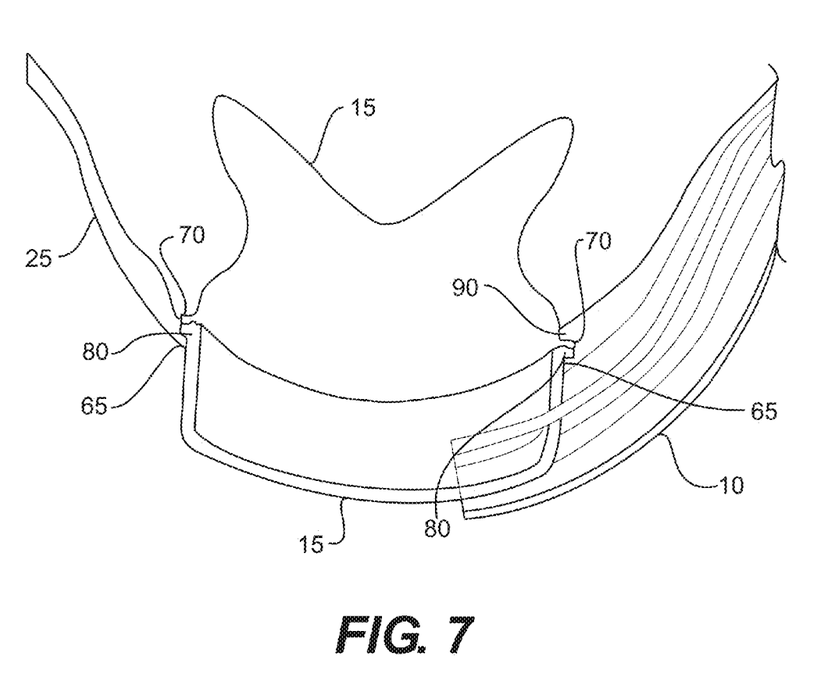
FIG. 7 is a cross-sectional view of the FIG. 5A embodiment.

FIG. 6 is a cross-sectional view of the FIG. 5A embodiment along the line A-A. This figure aids in viewing the lip 70 of the nasal interface in cooperation with the back portion 90 of the ledge 75. FIG. 7 is a cross-sectional view of the FIG. 5A embodiment showing the molded air tube 10 within the base member 15. This figure shows the snap tabs 65 holding the lip 80 of the base member 15 against the lip 70 of the nasal interface 15 against the back portion 90 of the ledge 75.

Figure 10:
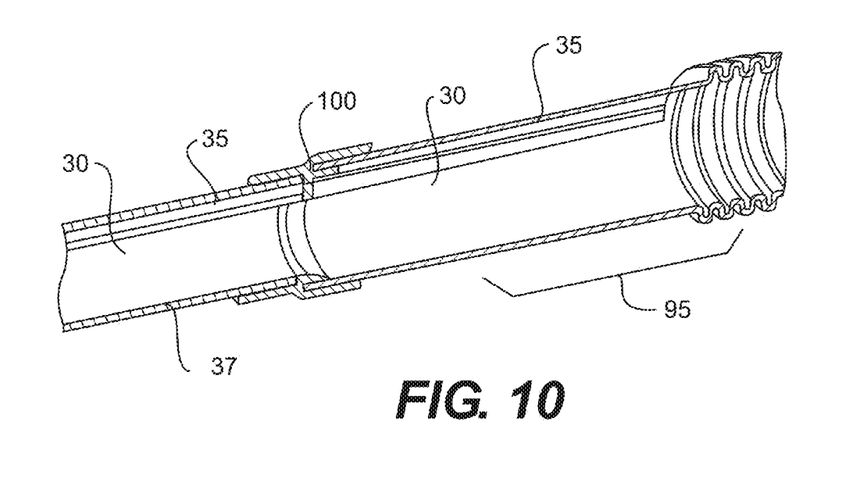
FIG. 10 is a cross-sectional view of a portion of an air tube and transition tube in accordance with the present disclosure.

FIG. 10 is a cross-sectional view of a portion of the molded air tube 10 and a transition tube 95 in accordance with the present disclosure. In the illustrated embodiment, the molded air tube 10 includes a transition section 37. A coupling portion 100 couples the transition tube 95 to the transition section 37 of the molded air tube 10. As shown in FIG. 10, the first lumen 30 of the transition tube 95 is coupled to the first lumen 30 of the transition section 37 of the molded air tube 10. Similarly, the second lumen 35 of the transition portion 37 of the molded air tube 10 is coupled to the second lumen 35 of the transition tube 95. As those skilled in the art will recognized any type of coupling could be used. The coupling should, however, couple the first and second lumens 30, 35 of the molded air tube 10 to the first and second lumens 30, 35 of the transition tube 95.

Figure 11:
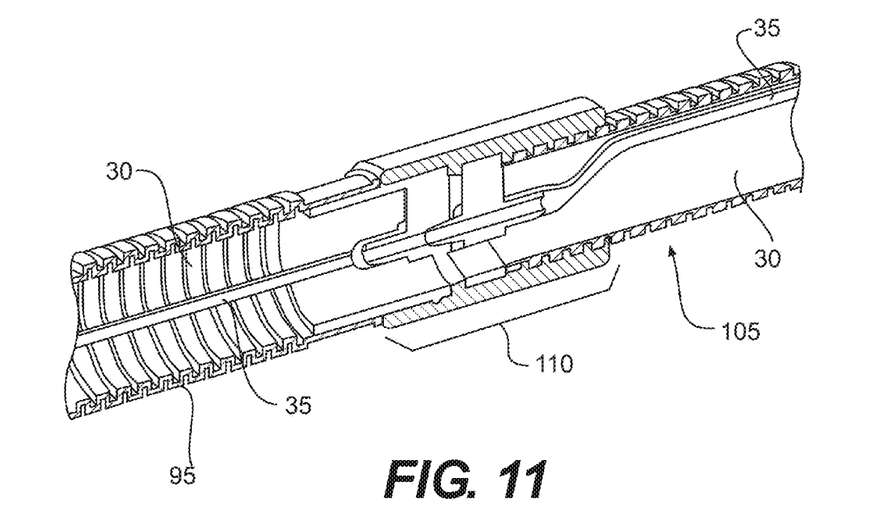
FIG. 11 is a cross-sectional view of a portion of a transition tube and a main tube in accordance with the present disclosure.

FIG. 11 is a cross-sectional view of a portion of a transition tube 95 and a main tube 105 in accordance with the present disclosure. Referring to FIG. 11, a coupler 110 couples the transition tube 95 and the main tube 105. the coupler couples the first and second lumens 30, 35 of the transition tube 95 to the first and second lumens of the main tube 105. The coupler 110 is discussed below. As seen in FIG. 11, the outside portion of the spiral/corrugated sections of the transition tube 95 and the main tube 105 have a flat outside portion. This is a preferred shape. The outside section need not have the illustrated flat shape.

Figure 8:
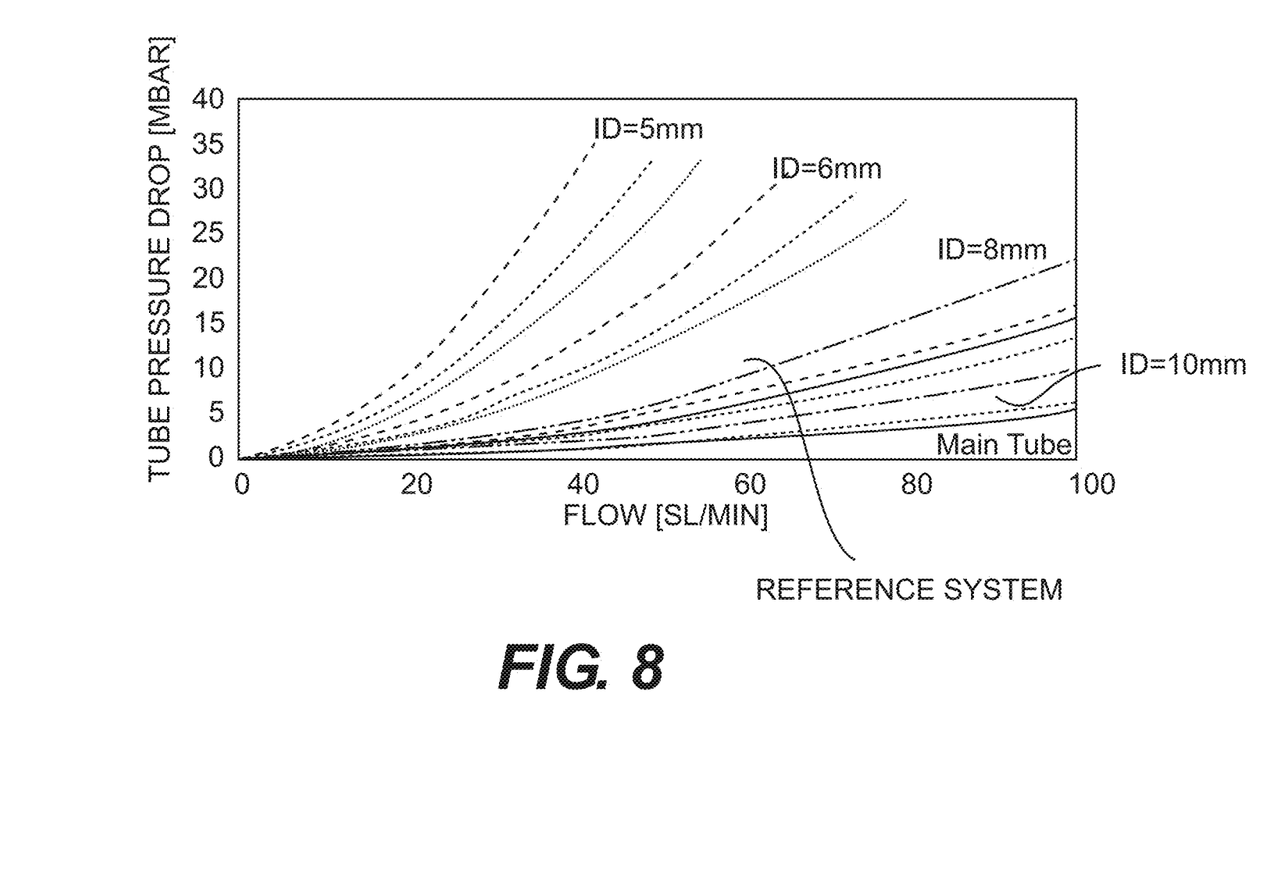
FIG. 8 is a graph showing flow data in accordance with the present disclosure.
Figure 9:
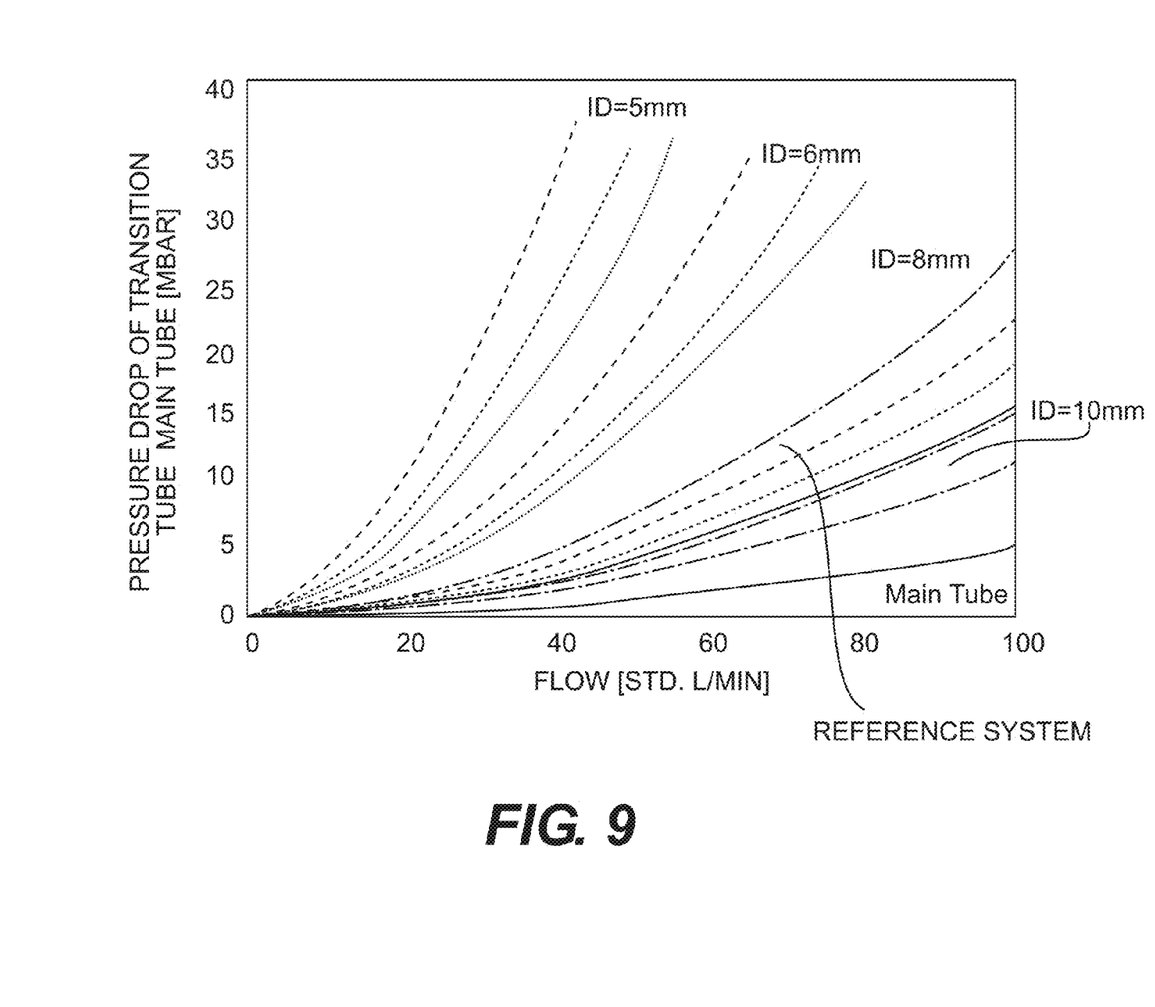
FIG. 9 is a graph showing flow data in accordance with the present disclosure.

FIGS. 8 and 9 are graphs showing flow data in accordance with the present disclosure. User comfort is a consideration in a nasal interface system. Accordingly, the diameter of air hoses, such as the molded air tube 10, transition tube 95 and main tube 105, is reduced in accordance with the disclosure. FIG. 8 shows the pressure drop of the main tube 105 for various diameters of the inner lumen 30. FIG. 8 shows that the pressure drop noticeably increases for diameters less than 8 mm. Thus, it is preferable from a speed of control and air source power to use a diameter of around 8 mm or more. FIG. 9 shows the pressure drop for the transition tube 95 and main tube 105. As in FIG. 8, there is a noticeable pressure drop increase for diameters less than 8 mm.

Figure 12A:
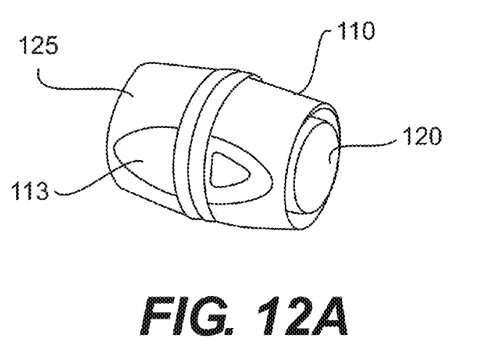
FIGS. 12A-12E illustrate a coupler in accordance with the present disclosure.
Figure 12B:
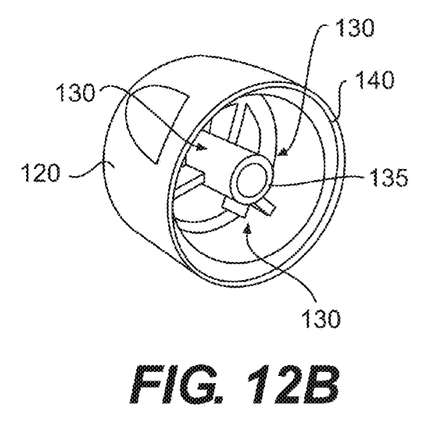

FIGS. 12A-12E illustrate a coupler in accordance with the present disclosure. FIG. 12A is a perspective view of the coupler 110 shown in FIG. 11. The flattened portions 115 aid in allowing a user to twist the first section 120 relative to a second section 125 of the coupler 110. In this illustrated embodiment of a coupler, the first section 120 includes a set of conic hooks 130 spaced about an inner lumen 135. While FIG. 12B shows three symmetrically spaced conic hooks 130, any suitable number could be used. As shown in FIG. 11, the inner lumen 135 couples to the second lumen 35. The first section 120 also includes a lip 145.

FIG. 12 C illustrates a perspective view of the section 125 of the coupler 110. The second section 125 includes a set of conic clamps 150. The number and spacing of conic clamps 150 should match that of the conic hooks 135. The second portion 125 includes a mating inner lumen 155. As shown in FIG. 11, and FIGS. 12D and 12E, the mating inner lumen 155 engages the inner lumen 135 of the first portion 120. This mating couples the second lumens 35 of the transition tube 95 and the main tube 105 as shown in FIG. 11. The conic hooks 130, inner lumen 135 could be positioned on the second portion 125, in which case, the conic clamps 150 and mating inner lumen would be positioned on the first portion 120. To join the first and second sections 120, 125, the conic clamps 155 are positioned between the conic hooks 130; and the first and second sections 120, 125 rotated relative to each other so that the conic clamps 155 engage the conic hooks 130 as shown in FIGS. 12D and 12E. The transition tube 95 and the main tube 105 can be inserted into either of the first opening 160 or the second opening 165 shown in FIG. 12E.

Figure 12C:
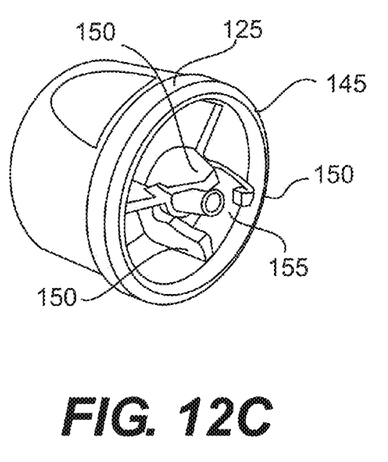
Figure 12D:
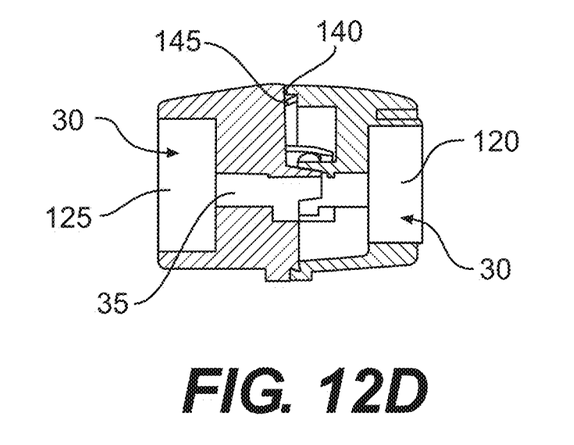
Figure 12E:
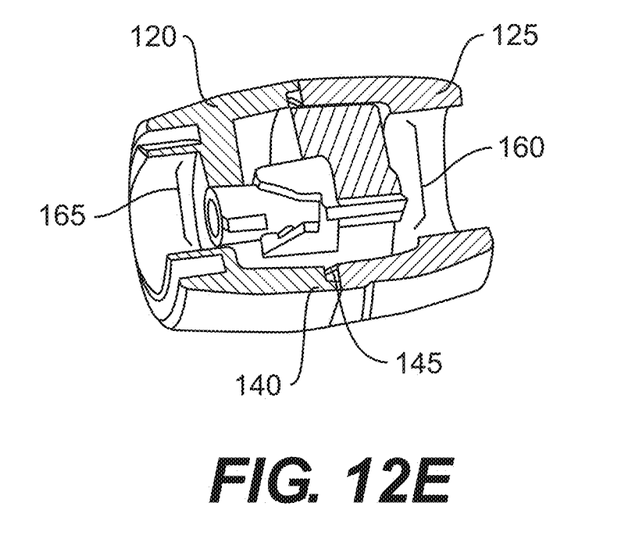

The first portion 120 includes a fence 140 that can engage a lip 145 of the second portion 125. This engagement aids in forming a sealing engagement so that air does not leak out of the coupler 110 from the first lumen 30.

Having thus described the invention of the present application in detail and by reference to embodiments thereof, it will be apparent that modifications and variations are possible without departing from the scope of the invention defined in the appended claims.

What is claimed is:

1. A replaceable nasal interface system comprising:
   a molded air tube having a generally D-shaped cross section, and including first and second lumens;
   a base member operatively connected to and in fluid communication with the molded air tube;
   a nasal interface operatively connected to the base member;
   a transition tube operatively connected to the molded air tube, the transition tube including third and fourth lumens in fluid communication with the first and second lumens, respectively;
   a main tube including fifth and sixth lumens; and
   a coupler including a first section operatively connected to the transition tube and a second section operatively connected to the main tube, the coupler including a first passage for coupling the third lumen to the fifth lumen and a second passage for coupling the fourth lumen to the sixth lumen.

2. A replaceable nasal interface system according to claim 1, wherein the coupler includes a set of conical hooks and a corresponding set of conical clamps positioned to engage the set of conical hooks.

\* \* \* \* \*